United States Patent [19]

Piccardi et al.

[11] 4,258,202

[45] Mar. 24, 1981

[54] CYCLOPROPANECARBOXYLIC ACIDS AND ESTERS

[75] Inventors: Paolo Piccardi; Francesco Corda, both of Milan; Franco Gozzo, San Giuliano Milanese; Augusto Menconi, Milan, all of Italy

[73] Assignee: Montedison S.p.A., Milan, Italy

[21] Appl. No.: 15,104

[22] Filed: Feb. 26, 1979

[30] Foreign Application Priority Data

Feb. 28, 1978 [IT]  Italy ............................... 20714 A/78
Dec. 12, 1978 [IT]  Italy ............................... 31310 A/78

[51] Int. Cl.³ .......................................... C07C 69/743
[52] U.S. Cl. .............................. 560/124; 260/544 L; 424/305; 560/192; 560/227; 562/506
[58] Field of Search ......................... 560/124; 562/506

[56] References Cited

U.S. PATENT DOCUMENTS 4,153,626  5/1979  Tieman ........................... 260/465 D
4,183,948  1/1980  Huff .................................... 560/124

FOREIGN PATENT DOCUMENTS 858137  2/1978  Belgium .
2802962  7/1978  Fed. Rep. of Germany .
52-14749  2/1977  Japan .
52-22345  10/1977  Japan .

OTHER PUBLICATIONS

Elliott, Chem. Soc. Rev. 7, pp. 473–505 (1978).
Casida, "Pyrethrum The Natural Insecticide," pp. 86–91 (1973).
Elliott, ACS Symp. Series, 42, pp. 1–23, Washington (1977).
Briggs, Pest. Sci., 7, pp. 236–240 (1976).
Elliott, Pest. Sci., 6, pp. 537–542 (1975).
Elliott, Pest. Sci., 7, pp. 492–498 (1976).
Elliott, Pest. Sci., 7, pp. 499–502 (1976).
Lee, Pest. Sci., 7, pp. 258–266 (1976).

Primary Examiner—Natalie Trousof
Assistant Examiner—Michael Shippen
Attorney, Agent, or Firm—Morgan, Finnegan, Pine, Foley & Lee

[57] ABSTRACT

Cyclopropanecarboxylic acids and esters are disclosed, having the formula:

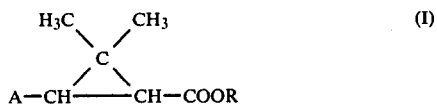

wherein
A=CF$_3$—C≡C—;

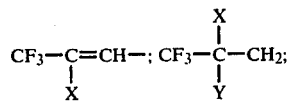

X=H, F, Cl, Br; Y=Cl, Br;
R=H, alkyl C$_1$-C$_4$

Compounds of formula I are intermediates for the preparation of insecticide compounds of the pyrethroid type.

3 Claims, No Drawings

CYCLOPROPANECARBOXYLIC ACIDS AND ESTERS

BACKGROUND OF THE INVENTION

The research of new derivatives of 2,2-dimethyl-cyclopropanecarboxylic acid gets an impulse by the fact that 2,2-dimethyl-3-isobutenyl-cyclopropanecarboxylic acid (chrysanthemic acid) esterified with a retronolone (2-alkenyl-3-methyl-cyclopent-2-en-4-olone), constitutes pyrethrum, an insecticide of a natural origin edowed with very positive characteristics such as for instance a high and fast insecticide action by contact on winged insects, and a low toxicity on mammals by mouth together with a negligible dermic toxicity.

However, the particular structure of the molecule makes pyrethrum easily degradable and therefore makes its action non-persistent, this latter characteristic not allowing its use for the protection of agricultural cultivations, thus limiting its use only for indoor applications.

Part of the research of new synthetic pyrethroids, that is, of substances which, by recalling the structure of pryethrum, are equally endowed with both a high insecticide activity as well as with a very low toxicity for mammals while showing, however, improved stability characteristics, has been directed towards the study of new derivatives of 2,2-dimethyl-cyclopropanecarboxylic acid.

There are known many derivatives substituted in position 3 of the cyclopropyl ring (see, for instance, Synthetic Pyrethroids (M. Elliot Ed.) ACS Symposium Series No. 42, Washington 1977). However, the most promising, from the point of view of the stability, are those derivatives that carry in position 3 a β, β-dihalovinyl group (J. Farkas et al., Chem. Listy 52, 688 (1958); M. Elliott et al., Nature (London) 246, 169 (1973); M. Elliott et al., J. Chem. Soc., Perkin 1, 1974, 2470).

DESCRIPTION OF THE INVENTION

The present invention concerns new derivatives of 2,2-dimethyl-cyclopropanecarboxylic acid having the general formula:

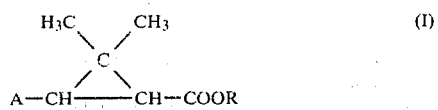

wherein:
$R = H$, alkyl $C_1-C_4$;
$A = CF_3-C|C-$;

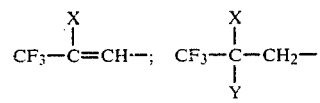

(wherein $X = H, F, Cl, Br$ and $Y = Cl, Br$).

The compounds object of this invention are intermediates useful for the synthesis of new pesticides, and, in particular, of new pyrethroids endowed with an activity superior than that of the known pyrethroids, as described in the copending patent application having Serial No. 15,105, filed February 26, 1979.

A process for the preparation of the derivatives of general formula (I), which forms another of this invention, is conducted starting from polyfluorohalogenated ethanes of the formula:

$$CF_3-C(X)Y_2$$

(wherein X and Y have the same meanings as those reported for general formula (I) and develops according to the reactions reported in Scheme 1.

Scheme 1 (R, X and Y have the meanings previously indicated)

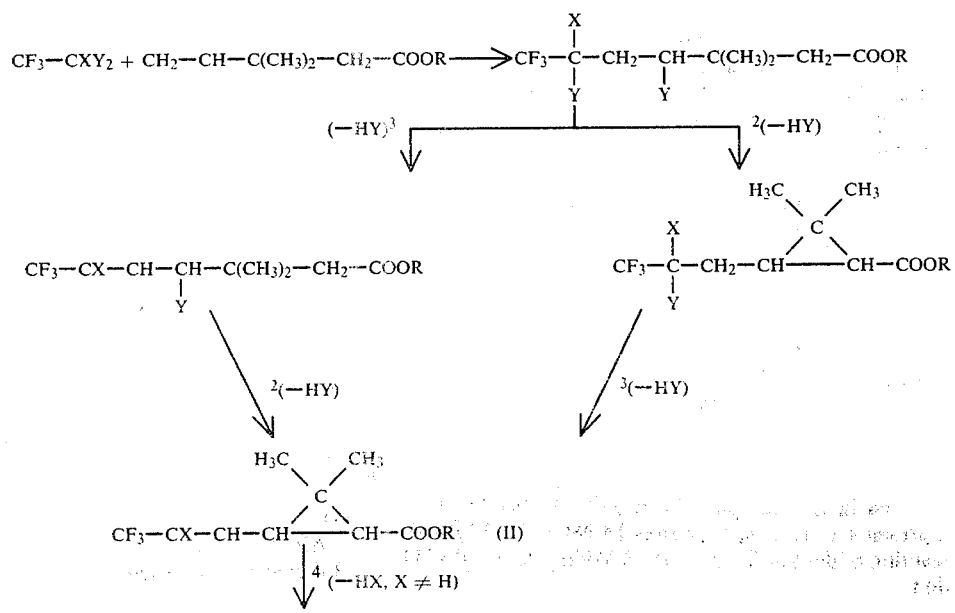

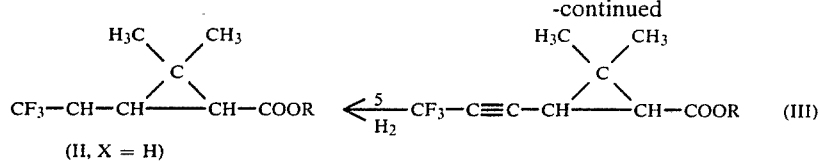

The process reported in Scheme 1 consists of the following stages:

(1) Addition of a compound of formula $CF_3$—$CXY_2$ to the double bond of an ester of 3,3-dimethyl-4-pentenoic acid, in the presence of radical reaction promoters, according to the equation:

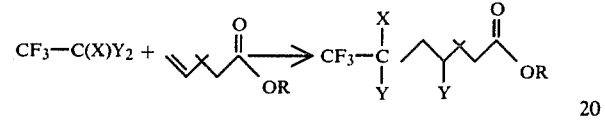

(2) Cyclization of the adduct thus obtained in the presence of a base:

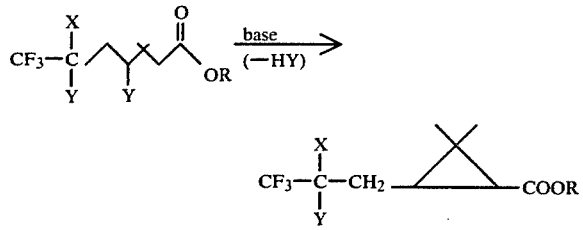

(3) Dehydrohalogenation by further treatment with a base:

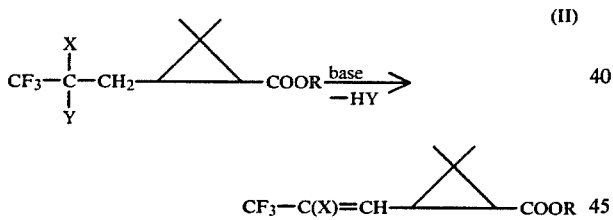

Depending on the conditions under which the last two reactions are carried out and on the nature of the halogen Y, stage 3 may be achieved as stage 2 goes on, or it may precede it according also the following sequences:

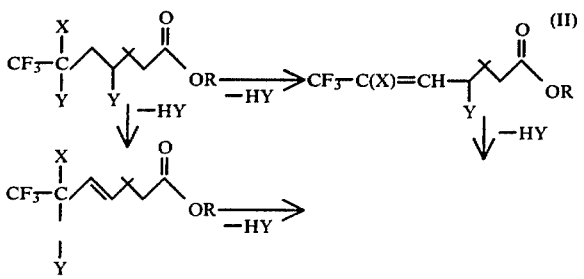

When in the compounds of general formula II, X represents a halogen, they may be subjected to further reaction of dehydrohalogenation according to the equation:

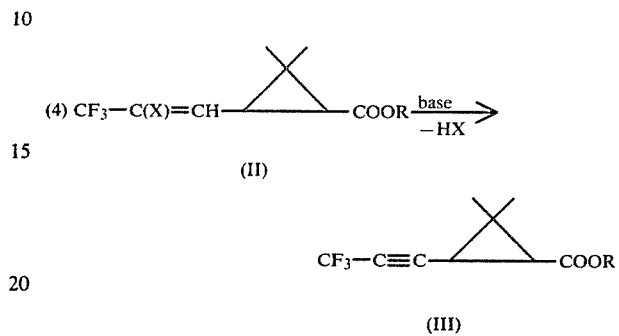

Also this latter reaction, if desired, may be carried out together with stages 2 and 3, without isolating the compounds of general formula II.

(5) Compounds of formula II wherein X=H can also be obtained by catalytic hydrogenation of compounds of formula III, using, for example, hydrogen and a poisoned Palladium catalyst.

The starting compounds of the type $CF_3$—$C(X)Y_2$ are all known products, easily obtainable from commercially available halogenated polyfluoroethanes, by means of known rearrangement reactions.

Following are a few examples of compounds of the type $CF_3$—$C(X)Y_2$:

$CF_3$—$CFBr_2$
$CF_3$—$CBr_3$
$CF_3$—$CClBr_2$
$CF_3$—$CHClBr$
$CF_3$—$CCl_3$

Suitable promoters of addition reaction (1) are organic peroxides such as tert-butyl peroxide, benzoyl peroxide or diacetyl peroxide; azoderivatives, such as, for instance, azo-bis-isobutyrronitrile; complexes containing transition metal salts, such as, for instance, those formed by iron salts or copper salts with aliphatic amines, or again, Redox-transfer systems. Reaction (1) is conducted by reacting the polyhalogeno-ethane, in the presence of catalytic quantities of one of the above cited radical reaction promoters, with an ester of 3,3-dimethyl-pentenoic acid, preferably in a molar ratio of polyhalogeno-ethane/ester greater than 1, at temperatures comprised between 50° and 200° C. The reaction may be conveniently carried out in an autoclave, at autogeneous pressure or at atmospheric pressure, in inert solvents at reflux temperature. Cyclization reaction (2) is achieved by the action of a strong base such as, for instance, an alkaline alcoholate or sodium hydride, in a polar solvent and at a temperature comprised between −20° and +50° C.

A prolonged treatment with the same base or at temperature conditions slightly more severe may cause the further dehydrohalogenation according to equation (3) and, when X is a halogen atom, according to equation (4).

Alternatively, the reaction for the elimination of the HY acid may be carried out either before or after the cyclization stage, by the action of inorganic bases or of halogenhydric acid-accepting amines.

The compounds prepared according to the thus described process are, in general, ethyl or methyl esters from which there are easily obtained the corresponding acids by conventional hydrolysis reactions.

When the reactions for the elimination of HY acids and/or of HX acid are carried out with inorganic bases such as sodium or potassium hydroxide, there occurs at the same time the hydrolysis of the ester group so that, by successive acidification, the compounds are obtained directly in the form of free acid.

Compounds of general formula I can also be prepared according to another process, and this forms a further object of this invention, which has as a first stage the addition of a compound of formula: $CF_3—CXY_2$ to an ester of 2-alcoxycarbonyl-3,3-dimethyl-4-penteneoic acid of the formula:

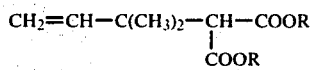

and that develops according to different ways, depending on the A substituent that one wishes to get in position 3 of the cyclopropylic ring.

The starting compound (2-alcoxycarbonyl-3,3-dimethyl-4-pentenoic ester) can easily be obtained by the reaction of 3-chloro-3-methyl-butene-1 with a malonic ester (Belgian Pat. No. 851,524).

In the following scheme 2 there have been summarized the steps that lead to the obtaining of the compounds of general formula I according to this second process.

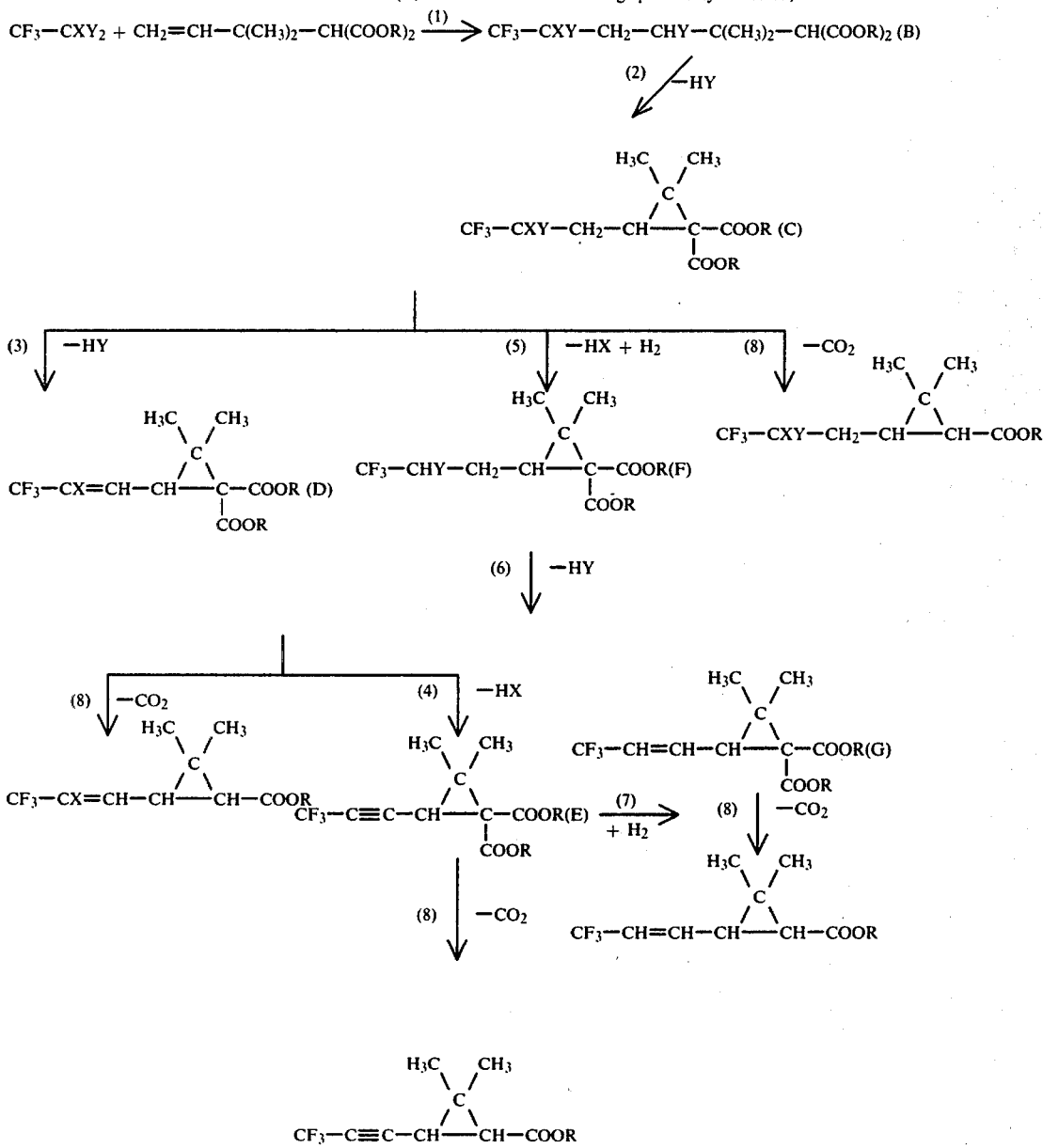

The various steps summarized in scheme 2 will now be explained in detail.

Reaction 1

Reaction 1 is conducted in the presence of promoters of radical reactions such as organic peroxides, for instance, tert-butyl peroxide, benzoyl peroxide or diacetyl peroxide; azo-derivatives such as azo-bis-isobutyronitrile, complexes containing salts of transition metals such as for instance those formed by iron or copper salts with aliphatic amines, or redox-transfer systems.

Reaction (1) is conducted by reacting, in the presence of catalytic quantities of one of the above cited radical reaction promoters, polyhalogenethane of the formula $CF_3$—$CXY_2$, with an ester of 2-alcoxycarbonyl-3,3-dimethyl-4-pentenoic acid, preferably in a molar ratio of polyhalogenoethane/ester of greater than 1, at temperatures comprised between 50° and 200° C.

The reaction may be conveniently carried out in an autoclave, under an autogeneous pressure or under atmospheric pressure, in inert solvents at reflux temperature.

Some examples of compounds of the $CF_3$—$C(X)Y_2$ type are:

$CF_3$—$CFBr_2$
$CF_3$—$CBr_3$
$CF_3$—$CClBr_2$
$CF_3CHClBr$
$CF_3$—$CCl_3$

Reaction 2

Reaction 2 is carried out by treating the adduct obtained by reaction 1 (B, scheme 2), with an equivalent of an alkaline base ($NaHCO_3$, $Na_2CO_3$, $K_2CO_3$, KOH, NaOH, $C_2H_5ONa$ ), in an organic solvent.

Thereby is obtained the diester of 1,1-cyclopropanedicarboxylic acid indicated by the letter (C) in scheme 2.

Starting from compound (C) one can follow several ways to modify the polyhalogenated chain in position 3 of the cyclopropylic ring and for carrying out the decarboxylation.

Reaction 3

The cyclopropanderivative obtained in step 2 is dehydrohalogenated by treating with one equivalent of an alkaline base, this latter being preferably a sodium alcoholate.

Optionally, the same type of intermediate may be obtained directly starting from the adduct described in step 1, by treatment with two equivalents of an alkaline base. Thereby is obtained the cyclopropandicarboxylate indicated by the letter (D).

Reaction 4

Compound (D) is further dehydrohalogenated (when X=Cl, Br) by treatment with an excess of a base, preferably an alkaline alcoholate, or by $NaNH_2$ in an organic solvent. Thereby is obtained the intermediate (E).

Reaction 5

Cyclopropandicarboxylate (C) is subjected to hydrogenolysis by the reaction of zinc powder in hydrochloric acid, in acetic acid or in methyl- or ethyl alcohol, thereby obtaining intermediate (F).

This reaction is carried out when X=Cl, Br, and results in the introduction of a hydrogen atom (X=H) in place of a halogen.

Reaction 6

Intermediate (F) is subjected to dehydrohalogenation under the same reaction conditions of reaction 3, thereby obtaining intermediate (G) which can be also obtained by catalytic hydrogenation (Reaction 7) of the triple bond of the chain in position 3 of the cyclopropylic ring of intermediate (E). The catalytic system used in Reaction 7 may be chosen from amongst those conventionally used for selective reductions of the triple bond to double bond, such as, for instance:

hydrogen on poisoned palladium catalyst;
$Na/NH_3$ liquid;
hydroboration followed by hydrolysis with aliphatic acids (Tetrahedron 1977, 33, page 1845).

By means of the reactions described so far there are obtained cyclopropandicarboxylates (C,D,E,F,G) which already carry in position 3, the polyhalogenated chains corresponding to the different meanings of substituent A in general formula I. From these, by decarboxylation (Reaction 8) there are obtained the compounds of general formula I.

Reaction 8

The intermediates (C,D,E,F,G) are subjected to decarboxylation under one or the other of the following conditions:

(8a) total or partial hydrolysis with acids or alkali in alcohol, followed by heating of the corresponding acids in neutral or basic organic solvents, at temperatures comprised between 100° and 250° C.

(8b) Hydrolysis as in (8a), followed by heating in quinoline in the presence of copper, at temperatures comprised between 100° and 250° C.

(8c) Heating in aprotic polar solvents such as dimethylsulphoxide in the presence of alkaline halides or cyanides, and of stoichiometric quantities of water (2 equivalents). Thus there were obtained compounds of general formula I in the form of carboxylic acids (R=H), for which, if desired, it is possible to prepare the corresponding esters by means of conventional esterification reactions, or in the form of esters from which, if desired, it is possible to prepare the corresponding acids by means of conventional hydrolysis reactions.

In Table 1 are summarized the reactions which lead to the different compounds falling under general formula I according to the process reported in scheme 2.

TABLE 1

Reactions for the preparation of compounds of the formula:

$$\begin{array}{c} H_3C \diagdown \diagup CH_3 \\ C \\ \diagup \diagdown \\ A-CH-\!\!\!-\!\!\!-CH-COOR \end{array}$$

(R=H, lower alkyl)

| Substituent A | Reactions |
|---|---|
| $CF_3$—C≡C— | 1 - 2 - 3 - 4 - 8 |
| $CF_3$—CX=CH— | 1 - 2 - 3 - 8 |
| $CF_3$—CH=CH— | $\begin{cases} 1 - 2 - 5 - 6 - 8 \\ 1 - 2 - 3 - 4 - 7 - 8 \end{cases}$ |
| (X=H) | |
| $CF_3$—CXY—$CH_2$ | 1 - 2 - 8 |

Following the procedures hereinabove described, compounds of general formula I reported in Table 2 were prepared.

TABLE 2

Compounds of general formula I.

| Compound | Formula | Characterization |
|---|---|---|
| a | CF$_3$—CF=CH—CH⟨C(CH$_3$)$_2$⟩CH—COOC$_2$H$_5$ (cyclopropane) | MS[a]<br>(C$_{11}$H$_{14}$F$_4$O$_2$)<br>254(M$^+$, 1,68%)<br>226(M$^+$—C$_2$H$_4$)<br>209(M$^+$—CH$_3$CH$_2$O)<br>185(M$^+$—CF$_3$)<br>181(M$^+$—COOC$_2$H$_5$, 100%) |
| b | CF$_3$—CFBr—CH$_2$—CH⟨C(CH$_3$)$_2$⟩CH—COOC$_2$H$_5$ | MS[a]<br>(C$_{11}$H$_{15}$F$_4$BrO$_2$)<br>334–336(M$^+$, 0.16%, 0.24%)<br>289–291(M$^+$—CH$_3$CH$_2$O)<br>255 (M$^+$—Br)<br>247,249,227,209) |
| c | CF$_3$—CF=CH—CH⟨C(CH$_3$)$_2$⟩CH—COOH | R.I.[b]<br>n$_D^{20}$ = 1.4180 |
| d | CF$_3$—CBr=CH—CH⟨C(CH$_3$)$_2$⟩CH—COOC$_2$H$_5$ | MS[a]<br>(C$_{11}$H$_{14}$F$_3$BrO$_2$)<br>314–316 (M$^+$, 0.15%, 0.16%)<br>269–271 (M$^+$—CH$_3$CH$_2$O)<br>241–243 (M$^+$—COOC$_2$H$_5$)<br>235(M$^+$—Br)<br>207(M$^+$—C$_2$H$_4$Br) |
| e | CF$_3$—CBr$_2$—CH$_2$—CH⟨C(CH$_3$)$_2$⟩CH—COOC$_2$H$_5$ | MS[a]<br>(C$_{11}$H$_{15}$F$_3$Br$_2$O$_2$)<br>394–396–398(M$^+$,3.4%, 5.9%, 3.4%)<br>313–315(M$^+$—Br)<br>314–316(M$^+$—HBr) |
| f | CF$_3$—C≡C—CH$_A$⟨C(CH$_3$)$_2$⟩CH$_B$—COOCH$_2$CH$_3$ (trans isomer) | MS[a]<br>(C$_{11}$H$_{13}$F$_3$O$_2$)<br>234(M$^+$,0.15%)<br>206(M$^+$—C$_2$H$_4$)<br>189(M$^+$—CH$_3$CH$_2$O)<br>161(M$^+$—COOC$_2$H$_5$)<br>141(M$^+$—C$_3$F$_3$)<br>NMR[c] (δ, ppm)<br>1.23 (t, 3H,CH$_3$—CH$_2$)<br>1.3 (6H, geminal methyls)<br>1.7–2.1(m,2H,H$_A$ + H$_B$)<br>4.1 (q,2H,CH$_2$—CH$_3$) |
| g | CF$_3$—CCl=CH$_C$—CH$_A$⟨C(CH$_3$)$_2$⟩CH$_B$—COOC$_2$H$_5$ | NMR[c] (δ, ppm)<br>1.2–1.4(9H, geminal methyls and CH$_3$—CH$_2$)<br>1.5–2.8(2H,H$_A$ + H$_B$)<br>4.06–4.12(q, 2H, CH$_3$—CH$_2$)<br>5.5–7(1H,H$_C$) |
| h | CF$_3$—C≡C—CH$_A$⟨C(CH$_3$)$_2$⟩CH$_B$—COOC$_2$H$_5$ | NMR[c] (δ, ppm)<br>1.28 (t,3H,CH$_3$—CH$_2$)<br>1.3–1.45(6H, geminal methyls)<br>1.7–2.15(m,2H,H$_A$ + H$_B$)<br>4.15 (q,2H,CH$_2$—CH$_3$)<br>IR[d] (cm$^{-1}$)<br>2250 (C≡C)<br>1820 (C=O) |
| i | H$_D$(CF$_3$)C=C(H$_C$)—CH$_A$⟨C(CH$_3$)$_2$⟩CH$_B$—COOCH$_2$—CH$_3$ (trans isomer) | NMR[c] (δ, ppm)<br>1.28(t,3H,CH$_3$—CH$_2$)<br>1.24(6H, geminal methyls)<br>1.65(d,1H,H$_B$)<br>2.4(m,1H,H$_A$)<br>4.15(q,2H,CH$_2$—CH$_3$)<br>5.75(m,2H,H$_C$ + H$_D$)<br>J(H$_A$—H$_B$) = 5 HZ<br>J(H$_A$—H$_C$) = 9 HZ<br>J(CH$_2$—CH$_3$) = 7 HZ<br>[19F NMR[e] 59.5(d,3F,CF$_3$)<br>IR[d] (cm$^{-1}$)<br>1650 (C=C), no bands at 2260 (C≡C)<br>mp[f] = 49–50° C. |
| j | CF$_3$—CH=CH—CH⟨C(CH$_3$)$_2$⟩CH—COOH | |

TABLE 2-continued

Compounds of general formula I.

| Compound | Formula | Characterization |
|---|---|---|
| k | $CF_3-CHCl-CH_2-CH_A$ —— $CH_B-COOCH_2-CH_3$ with geminal $H_3C$, $CH_3$ on middle C | $NMR^{(c)}$ ($\delta$, ppm)<br>1.2(m,9H, geminal methyls + $CH_3-CH_2$)<br>1.7-2.7(m,2H, $H_A + H_B$)<br>1.5-2.2(m2H, $CH_2-CHCl$)<br>4.1(m + q, 3H, CHCl + $CH_2-CH_3$) |
| l | $CF_3, H_D$ $C=C$ $H_C$, $H_3C$, $CH_3$ $-COOCH_2-CH_3$ $H_A$ $H_B$ | $NMR^{(c)}$ ($\delta$, ppm)<br>1.25 (t,3H, $CH_3-CH_2$)<br>1.3 (s,6H, geminal methyls)<br>1.8 ⎫<br>1.85 ⎭ (d,d,1H,$H_B$)<br>2.15 (d,d,1H,$H_A$)<br>4.15 (q,2H,$CH_2-CH_3$)<br>6 (m,2H,$H_C + H_D$)<br>J ($H_A-H_B$) = 5 HZ<br>J ($H_A-H_C$) = 8 HZ<br>J ($CH_2-CH_3$) = 7 HZ<br>R.I.$^{(b)}$<br>$n_D^{23}$ = 1.4206 |

Notes for Table 2
$^{(a)}$MS = Mass-spectroscopic data, only the main ions are reported.
$^{(b)}$R.I. = Refraction index.
$^{(c)}$NMR = $^1$H Nuclear Magnetic Resonance spectroscopic data NMR spectra were recorded using $CDCl_3$ as solvent and TMS as internal standard.
s = singlet,
d = doublet,
t = triplet,
q = quartet,
m = multiplet;
J = coupling constant.
$^{(d)}$IR = Infra-Red spectroscopic data, only the more significant bands are reported.
$^{(e)19}$F NMR spectra were recorded using $CDCl_3$ as solvent and $CFCl_3$ as internal standard; d = doublet.
$^{(f)}$the melting point has not been corrected.

Compounds of general formula I are intermediate in the synthesis of pyrethroid type insecticides. These latter are esters of the carboxylic acids of formula I with particular alcohols and can be prepared by transforming the acids or esters of formula I into the corresponding acyl halides, which are made then to react with the suitable alcohols.

Pyrethroids obtained from the compounds of this present invention are described in the copending patent application having Ser. No. 15,105, filed February 26, 1979.

The particular structure of the compounds of general formula I admits the existence of various geometrical and configurational isomers whose existence derives from the presence of the following factors:

(i) the asymmetric nature of the carbon atoms 1 and 3 of the cyclopropyl ring (enantiomers);
(ii) relative spacial disposition of the COOR group and of substituent A with respect to the plane defined by the cyclopropyl ring (cis or trans);
(iii) cis or trans isomery of the substituents present on the double bond in the case in which $$A = CF_3 - \underset{X}{C} = CH -.$$

The separation of the various racemic mixtures in the various stereoisomers and in their enantiomers may be obtained by following known chemical techniques, such as, for instance, chromatographic methods and, respectively, precipitations of salts with optically active bases. There falls under the spirit of this invention the isolation and use of all steric and/or configurational isomers obtainable from mixtures prepared according to the processes hereinabove indicated, as well as the use of the mixtures themselves and of those derived from their partial or complete separation in stereoisomers.

DESCRIPTION OF THE SPECIFIC EMBODIMENT

In the following will now be given some examples in order to illustrate further the invention.

Example 15, taken from the copending patent application, Ser. No. 15,105, filed February 26, 1979, describes the use of the compounds of the present invention in the synthesis of new pyrethroids.

EXAMPLE 1

Preparation of the intermediate ethyl 3,3-dimethyl-4,6-dibromo-6,7,7,7-tetrafluoro-heptanoate Into a 200 ml autoclave were loaded, in a nitrogen atmosphere, the following reactants: 17 g of ethyl ester of 3,3-dimethyl-4-pentenoic acid (0.105 mols); 55 g, of 1,1,1,2-tetrafluorodibromoethane (0.21 mols); 0.5 ml of ter-butylperoxide.

The autoclave was then immersed into an oil bath and mechanically shaken for 5 hours at a temperature of 120° C.

After cooling down, the content was diluted with 100 ml of $CH_2Cl_2$. This solution was then washed with $H_2O$ (3 times, 50 ml each time) containing small quantities of FeSO$_4$, then dried on anhydrous CaCl$_2$ and the solvent was then evaporated under vacuum. Thereby were obtained 43.3 g of raw product which was thereupon distilled under vacuum, gathering the fraction boiling at 97°–99° C. at a pressure of 0.25 mm Hg. There were obtained: 39 g of ethyl 3,3-dimethyl-4,6-dibromo-6,7,7,7-tetrafluoroheptanoate.

Elemental analysis:
Bromine: calculated, 38.41%; found: 37.83%

EXAMPLE 2

Preparation of ethyl ester of 2,2-dimethyl-3-($\beta$-fluoro-$\beta$-trifluormethyl-vinyl)-cyclopropancarboxylic acid and of free acid To a solution of ethyl 3,3-dimethyl-4,6-dibromo--6,7,7,7-tetrafluoroheptanoate (25 g, 0.06 mols), obtained as described in Example 1, in ethanol (50 ml) was added at a temperature comprised between 23° and 32° C. and under constant stirring, a solution of sodium ethylate (0.132 mols) in ethanol (150 ml).

Once the addition had been completed, the resulting solution was maintained at room temperature for 3 hours. Thereupon 50 ml of the solution were withdrawn and were concentrated to a reduced volume. The resulting solution was then poured into water and ice. It was then extracted with CH$_2$Cl$_2$ (50 ml) and the organic phase was washed with water to a neutral pH. Thereupon it was anhydrified with CaCl$_2$ and the solvent was removed under vacuum.

Thereby were obtained 3.6 g of a raw reaction product which, when analyzed by gas-chromatogrphy coupled with mass spectrometry, proved to be prevailingly composed of ethyl ester of 2,2-dimethyl-3-($\beta$-fluoro-$\beta$-trifluoromethyl-vinyl)cyclopropancarboxylic acid (compound a, Table 2) isolable from the raw product by column chromatography, and by about 20% of ethyl ester of 2,2-dimethyl-3-($\beta$-bromo-$\beta$,$\gamma$,$\gamma$,$\gamma$-tetrafluoropropyl)cyclopropancarboxylic acid (compound b, Table 2). The remainder of the ethanol solution, from which there had been drawn the aliquot of 50 ml, was treated with 6 g of KOH in an 85% concentration, in 30 ml of ethanol.

The reaction mixture was thereupon heated for 2 hours at reflux temperature in order to carry out the hydrolysis of the ester and in order to complete the dehydrobromidation of the $\beta$-bromo-$\beta$,$\gamma$,$\gamma$,$\gamma$-tetrafluoropyl group.

The reaction mixture was then concentrated to a reduced volume and poured into water and ice. The mixture was acidifed with diluted H$_2$SO$_4$, then extracted with CH$_2$Cl$_2$ (3 times, 50 ml each time) and the organic phase was washed with an aqueous solution of NaCl (2 times, 100 ml each time) and finally anhydrified with CaCl$_2$. The solvent was removed under vacuum and there were obtained 8 g of 2,2-dimethyl-3- ($\beta$-fluoro-$\beta$-trifluormethyl-vinyl)-cyclopropanecarboxylic acid in the form of a viscous oil of a straw-yellow color (compound c, Table 2).

EXAMPLE 3

Preparation of the ethyl 3,3-dimethyl-4,6,6-tribromo-7,7,7-trifluoro heptanoate intermediate Into a 200 ml autoclave were loaded, under a nitrogen atmosphere, the following reactants: 13 g of ethyl ester of 3,3-dimethyl-4-pentenoic acid (0.083 mols); 53 g of 1,1,1-trifluoro-2,2,2-tribromoethane (0.166 mols); 0.5 ml of tert-butyl peroxide.

The autoclave was thereupon immersed into an oil bath and mechanically shaken for 5 hours at a temperature of 120° C. and for 1 hour at 130° C. After cooling down, the content was diluted with 100 ml of methylene chloride. The solution was then washed with water (3 times, 50 ml each time), containing small quantities of ferrous sulphate, and anhydrified on CaCl$_2$. After removal of the solvent by evaporation, the raw product was distilled under vacuum, thereby gathering the fraction boiling at 117°–118° C. (at a pressure of 0.15 mm Hg), consisting of 31.3 g of ethyl 3,3-dimethyl-4,6,6-tribromo-7,7,7-trifluoro-heptanoate.

Elemental analysis:
Bromine: theoretical = 50.26%; found = 48.57%

EXAMPLE 4

To a solution of ethyl 3,3-dimethyl-4,6,6-tribromo-7,7,7-trifluoroheptanoate (4.7 g, prepared as described in Example 3 in ethanol (10 ml), was added, under stirring, a solution of sodium ethylate (0.022 mols) in ethanol (60 ml), the temperature being maintained at between 19° C. and 23° C.

The resulting solution was maintained at room temperature for 3 hours, until, that is, the gas-chromatographic control indicated that the starting ester had completely disappeared.

The solution was then concentrated to a reduced volume poured into water and ice and then extracted with CH$_2$Cl$_2$(3×40 ml). The organic solution was then washed with water until achieving a neutral pH, and finally anhydrified with CaCl$_2$. The solvent was then removed under vacuum, thereby obtaining 2.6 grams of raw product which is separated by column chromatography in 4 fractions. Three of these fractions, analyzed by gaschromatography and identified by gas-chromatography coupled with mass spectrometry, proved to have the following compositions:

Fraction I (0.3 g) = ethyl ester of 2,2-dimethyl-3-($\beta$-bromo,$\beta$-trifluoromethyl-vinyl)-cyclopropancarboxylic acid (compound d, Table 2;

Fraction II (0.5 g) = mixture consisting of about 55% of compound d, about 20% of the compound forming fraction III (compound f) and of about 25% of ethyl ester of 2,2-dimethyl-3-($\beta$,$\beta$-dibromo-$\gamma$,$\gamma$,$\gamma$-trifluoro-propyl)-cyclopropancarboxylic acid (compound e, Table 2);

Fraction III (0.6 g) = ethyl ester of 2,2-dimethyl-3-($\beta$-trifluoro-methyl-ethynyl)-cyclopropancarboxylic acid (compound f, Table 2).

EXAMPLE 5

Preparation of the ethyl 3,3-dimethyl-4,6,6-trichloro-7,7,7-trifluoro-heptanoate intermediate Into a 100 ml flask were loaded, under a nitrogen atmosphere, the following reactants:

7.8 g of ethyl ester of the 3,3-dimethyl-4-pentenoic acid (0.05 mols);
18.75 g of 1,1,1-trifluoro-trichloroethane (0.1 mols); 0.25 g of cuprous chloride; ,
3.5 ml of ethanolamine;
50 ml of tertbutyl alcohol.

The reaction mixture was thereupon heated for 10 hours at reflux temperature. After having been cooled down, the mixture was then evaporated under vacuum in order to remove the tertbutyl alcohol.

The residue, diluted with 50 ml of diethyl ether, was treated with diluted HCl until achieving an acid pH. The ether phase was then washed with water, neutralized with NaHCO$_3$, anhydrified on Na$_2$SO$_4$, and finally the solvent was removed under vacuum in order to yield as a residue 17.2 g of an oil which, by distillation under vacuum, yields 13.2 g of a fraction with boiling point comprised between 105° and 110° C. at 0.60 mm Hg., consisting of ethyl 3,3-dimethyl-4, 6,6-trichloro-7,7,7-trifluoroheptanoate (gas-chromatographic titre: 93%; theoretical Cl=30.96%, found Cl=30.36%).

The IR and NMR spectra of this product are consistant with the indicated structure.

EXAMPLE 6

Preparation of ethyl ester of the (±)-cis, trans,2,2-dimethyl-3-(β-chloro-,β-trifluoromethyl-vinyl)-cyclopropancarboxylic acid (mixture of isomers)

To a solution of 0.06 mols of sodium ethylate in 30 ml of absolute ethanol was added, at a temperature of −20° C., a solution of 11 g of the intermediate prepared according to Example 5 (0.03 mols) in 10 ml of ethanol. The reaction mixture was kept under stirring for 1 hour at 0° C. and, after left standing overnight, stirring was resumed for 2 hours at 50°-60° C.

After cooling down and filtering, from the sodium chloride thus formed (3.8 g), the solution was poured into water and ice, after which it was extracted with diethylether (3×30 ml). The ether extract, after washing with water and anhydrification on Na$_2$SO$_4$, was evaporated under vacuum to yield 8.1 g of an oily liquid which, according to the gas-chromatographic analysis followed by a characterization by mass-gas-chromatography, proved to consist prevailingly of the isomers of compound g (about 83%) and of a minor quantity (about 12%) of compound f. The I.R. spectrum of this mixture revealed the presence of absorptions characteristic of the double bond C═C ($\nu=1650$ cm$^{-1}$), of the triple bond C≡C ($\nu=2250$ cm$^{-1}$) and of the esteric C═O group ($\nu=1720$ cm$^{-1}$). By distillation under reduced pressure there was gathered the fraction with b.p.=105° to 115° C. at 23 mm Hg, consisting of 4.1 g of a color less oil whose I.R. and N.M.R. spectra showed to be consistant with the structure of ethyl ester of (±)-cis, trans-2,2-dimethyl-3-(β-chloro, β-trifluoromethyl-vinyl)-cyclopropanecarboxylic acid (a mixture of isomers of compound g, Table 2), n$_D^{20}$=1,4352.

EXAMPLE 7

Preparation of ethyl ester of (±)-cis, trans-2,2-dimethyl-3-(β-trifluoromethyl-ethynyl)-cyclopropanecarboxylic acid (mixture of isomers).

Into a well dried round bottomed flask of 250 ml holding capacity, equipped with a reflux condenser, 8 g of a suspension at 25% concentration of sodium-amide in Degussa oil under 50 ml of anhydrous benzene, were introduced. Then, at 0° C. under nitrogen atmosphere, the following reactants were added:

13.5 g of ethyl ester of 2,2-dimethyl-3-(β-chloro-β-trifluoromethyl-vinyl)-cyclopropanecarboxylic acid (mixture of isomers)
5 ml of tert-butanol
5 ml of anhydrous benzene.

The reaction mixture was kept at 15°-20° C. by cooling with an external ice-water bath until no more heat was evolved (about 1 hour). The reaction mixture was then heated at reflux temperature for 6 hours. Then, after cooling at room temperature, it was poured in 100 ml of a 2 N hydrogen chloride aqueous solution. The organic phase was then separated, washed with water to a neutral pH, dried on anhydrous Na$_2$SO$_4$ and filtered. The organic solvent was then removed under vacuum, yielding 12.5 g of raw product which was distilled on a Vigreux column (10 cm high), collecting the fraction boiling at 93°-99° C. (35 mm Hg) and consisting of the desired product, (Compound h, Table 2).

By the comparison between the NMR data (see Table 2) of compound h and of compound f, it appears that the latter is the trans isomer.

EXAMPLE 8

Preparation of ethyl ester of (±)-trans-2,2-dimethyl-3-(β--trifluoromethyl-Z-vinyl)-cyclopropanecarboxylic acid (compound i, Table 2) and of the corresponding free acid.

Into a round bottomed flask of 500 ml holding capacity, under nitrogen atmosphere, were introduced:
11.5 g of ethyl ester of 2,2-dimethyl-3-(β-trifluoromethyl-ethynyl-cyclopropanecarboxylic acid (compound f)
200 ml of n-hexane
2 g of Palladium supported on Calcium carbonate (Pd/CaCO$_3$), poisoned by Lead (prepared according to Organic Synthesis, Coll. Vol. V, 880, John Wiley & Son, 1973).

The flask was then connected to a hydrogenation apparatus and the content of the flask was vigorously stirred for some hours until no more hydrogen was absorbed.

The reaction mixture was then filtered on Celite, and the solvent was evaporated obtaining 10.5 g of raw product that was distilled at reduced pressure.

The fraction boiling at 88° C. (16 mm Hg) was gathered and, when analyzed by IR and NMR spectroscopy, proved to be compound i (purity:≧90% by GLC, gas-liquid chromatography). To 7 g of compound i were added 4 g of KOH (85% conc) and 50 ml of ethanol (95% conc). The whole was reflux heated for 4 hours. Most of the solvent was then evaporated and 50 ml of water were added. 10 g of an aqueous solution of sulphuric acid (1:1) were added to the resulting mixture which was then extracted with methylene chloride.

The organic phase was then dried on anhydrous Na$_2$SO$_4$, and filtered. By removing the solvent under vacuum, 5.9 g of an oil were obtained, which when crystallized in n-pentane, provides the corresponding carboxylic acid as a white solid (m.p. 49°-50° C.) (compound j, Table 2).

EXAMPLE 9

Preparation of ethyl ester of 2,2-dimethyl-3-(2-chloro-3,3,3-trifluoro-propyl)-cyclopropanecarboxylic acid Into a Pyrex glass tube for reactions under pressure were charged, under nitrogen atmosphere, the following reactants:

ethyl ester of 3,3-dimethyl-4-pentenoic acid (15.6 g, 0.1 mol)
1,1,1-trifluoro-chlorobromoethane (59.2, 0.3 mol)
ethanolamine (3 ml)

Cu Cl (0.6 g)

The glass tube was then flame sealed and shaken for obtaining an homogeneous mixture, then it was introduced in an autoclave containing water for about ⅔ of its volume. The autoclave was closed and heated at 120°-140° C. for 20 hours. After cooling down the glass tube was opened and the excess of 1,1,1-trifluorochlorobromoethane was distilled under vacuum.

The residue was collected with diethyl-ether, washed with an hydrogen chloride solution (2 N), then with water until a neutral pH was obtained and filtered.

The organic phase was dried on anhydrous $Na_2SO_4$ and the solvent was removed under vacuum. The residue was distilled at reduced pressure, gathering the fraction (20 g) boiling at 70°-75° C. (0.06 mm Hg) consisting of ethyl ester of 3,3-dimethyl-4-bromo-6-chloro-7,7,7-trifluoro eptanoic acid ($n_D^{24}$=1.4415, Elemental Analysis, IR and NMR spectra consistent with the assigned structure).

10 g of this intermediate were dissolved in 10 ml of absolute ethanol and the resulting solution was added at room temperature to a solution of sodium ethylate prepared by dissolving 1.5 g of sodium in 55 ml of absolute ethanol. The reaction mixture was then reflux heated for 1.5 hours, then the solvent was evaporated under vacuum and 100 ml of water were added to the residue.

The organic material was extracted with diethyl ether (3×75 ml). The organic phase was then washed with water to a neutral pH, dried on anhydrous $Na_2SO_4$ and the solvent was evaporated under vacuum. Thereby were obtained 6.3 g of ethyl ester of 2,2-dimethyl-3-(2-chloro-3,3,3-trifluoropropyl)-cyclopropane carboxylic acid as mixture of cis, trans-isomers (about 1:1) (compound k, Table 2).

EXAMPLE 10

Preparation of ethyl ester of (±)-cis, trans-2,2-dimethyl-3-
-(α-trifluoromethyl-E-vinyl)-cyclopropanecarboxylic acid 2.5 g of $C_2H_5ON$ a were dissolved at −15° C. in 80 ml of dimethylformamide. To this solution, a solution of 6.3 g of ethyl ester of (±)-cis, trans-2,2-dimethyl-3-(2-chloro-3,3,3-trifluoropropyl)-cyclopropanecarboxylic acid in 20 ml of dimethylformamide was added.

The reaction mixture was slowly heated from −15° C. to 0° C. in 3 hours, then 100 ml of water at 0° C. were added to it. The organic material was then extracted with diethyl ether (3×100 ml). The organic solution was then washed with water to a neutral pH and dried with anhydrous $CaCl_2$ and the solvent was removed under vacuum. Thereby were obtained 5 g of ethyl ester of (±)-cis, trans-2,2-dimethyl-3-(β-trifluoromethyl-E-vinyl)-cyclopropanecarboxylic acid as mixture of ci-trans isomers in about 1:1 ratio. (Compound 1, Table 2).

Th same reaction was carried out also at 0° C. for 15 hours. Thereby was obtained a product consisting for about 90% of the trans isomer, as evidence by the disappearance in the NMR spectrum of the signal at 1.85 ppm corresponding to the proton $H_B$ of the cis-isomer. (See Table 2).

EXAMPLE 11

Preparation of $CF_3$-CFBr-$CH_2$-CHBr-C($CH_3$)$_2$-CH($CO_2C_2H_5$)$_2$

Into a 250 ml Hastelloy C autoclave fitted with a balance rocker, under a nitrogen atmosphere, were introduced:

208 g of $CF_3$-$CFBr_2$ (0.8 mols)
91.2 g of $CH_2$=CH-C($CH_3$)$_2$—CH($CO_2Et$)$_2$ (0.4 mols)
6 ml of ditertbutyl peroxide.

The autoclave was heated up to 140° C. and maintained at this temperature for 2 hours. After cooling, the content was discharged and the excess of $CF_3$—$CFBr_2$ was removed by evaporation, after which the content of the autoclave was subjected to molecular distillation, gathering the fraction with b.p.=90° C. ($10^{-3}$ mm Hg) which consisted of 120 g of ethyl (1,1-dimethyl-2,4-dibromo-4,5,5,5-tetrafluoro) pentyl-malonate.

$N_D^{22°}$=1,45 13

I.R. analysis was consistent with the indicated structure.

Elemental analysis: C found=34.9%; theoret. C=34.5%, H found=4.2%; theoret. H=4.1%, F found=15.4%; theoret. F=15.6%, Br found=31.9%; theoret. Br=32.8%.

EXAMPLE 12

Preparation of $$CF_3-CFBr-CH_2-CH-\overset{\overset{\displaystyle CH_3\ \ CH_3}{\diagdown\diagup}}{\underset{\underset{\displaystyle CO_2C_2H_5}{|}}{C}}-CO_2C_2H_5 \text{ and of}$$

$$CF_3-CF=CH-CH-\overset{\overset{\displaystyle CH_3\ \ CH_3}{\diagdown\diagup}}{\underset{\underset{\displaystyle CO_2C_2H_5}{|}}{C}}-CO_2C_2H_5$$

48.8 g (0.1 mols) of ethyl (1,1-dimethyl-2,4-dibromo-4,5,5,5-tetrafluoro)-pentyl-malonate, prepared as described in Example 11, in 100 ml of anhydrous ethanol were added dropwise and under stirring to an ethanolic solution of sodium ethylate, prepared with 2.4 g of sodium and 100 ml of anhydrous ethanol.

Once the addition had been completed, from the mixture was drawn a sample which was then gas-mass analyzed, the results of which showed that the cyclization reaction had already been fully completed to give compound $$CF_3-CFBr-CH_2-CH-\overset{\overset{\displaystyle CH_3\ \ CH_3}{\diagdown\diagup}}{\underset{\underset{\displaystyle CO_2C_2H_5}{|}}{C}}-CO_2C_2H_5$$

Mass fragmentation:
($C_{14}H_{19}F_4BRO_4$):
406($M^+$),
327 ($M^+$—Br),
361 ($M^+$—$C_2H_5O$),
213 ($M^+$—$C_3F_4BrH_2$),
315
314

185
167
43

At this point there was added a further amount of sodium ethylate in ethanol (equal to the preceding one), and the reaction mixture was kept under stirring at 40° C. for 5 hours.

After neutralization with HCl, 1:1, and subsequent filtration, the solution was concentrated to a small volume, additioned with 200 ml of water and then extracted with $CHCl_3$ (2×150 ml). The chloroformic extract was then anhydrified on $CaCl_2$ and then evaporated to give 31.4 g of diethyl ester of 2, 2-dimethyl-3-($\beta$-fluoro-$\beta$-trifluoromethyl-vinyl)-cyclopropan-1, 1-dicarboxylic acid, $n_D^{22°} = 1.4303$

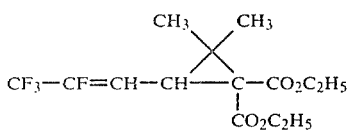

Mass fragmentation:
($C_{14}H_{18}F_4O_4$):
326 ($M^+$)
281 ($M^+ - C_2H_5O$)
253 ($M^+ - C_3H_5O_2$)
225 (253 — $C_2H_4$)
235
207
179
167
160
115

EXAMPLE 13

Preparation of

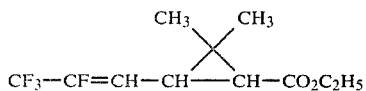

Into a flask immersed in an oil bath and fitted with a reflux condenser there were introduced, in a nitrogen atmosphere: 5 g of

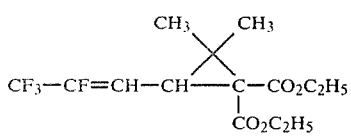

prepared as described in Example 12.
1 g of NaCl
12 ml of dimethylsulphoxide
0.6 ml of water The reaction mixture was then reflux-heated for 9 hours at 165°–167° C.

After cooling down, the gas-chromatographic analysis showed that the compound had formed with a conversion of 75% and with a cis/trans ratio on the ring of about 1:1.

EXAMPLE 14

Preparation of $CF_3\text{-}CCl_2\text{-}CH_2\text{-}CHCl\text{-}C(CH_3)_2\text{-}CH(CO_2C_2H_5)_2$ Into a Hastelloy-c autoclave, mechanically stirred, were introduced under a nitrogen atmosphere:
23 g of $CH_2=CH-C(CH_3)_2-CH(CO_2C_2H_5)_2$ (0,1 mol)
82.5 g of $CF_3-CCl_3$ (0,4 mol)
0.16 g of CuCl
3.5 g of ethanolamine.
115 ml of tertbutyl alcohol.

The autoclave was heated at 100° C. for 2 hours and then at 110° C. for another 7 hours.

After cooling down, the reaction mixture was filtered and, after removal of the excess of $CF_3CCl_3$ by evaporation, the solution was distilled at reduced pressure.

Thereby were gathered 20 g of a fraction with b.p. 105° C./0.05 mm Hg, consisting of ethyl (1,1-dimethyl-2,4,4-trichloro-5,5,5-trifluoro)-pentyl malonate.

IR (pure sample): 1720 and 1740 $cm^{-1}(C=O)$; other bands at: 1460, 1362, 1300, 1255, 1227, 1205, 1175, 1040 $cm^{-1}$.

Elemental analysis:
C(%) found 41.1 calc. 40.4
H(%) found 4.9 calc. 4.8
F(%) found 13.2 calc. 13.7
Cl(%) found 25.1 calc. 25.6

EXAMPLE 15

(The present example has for its purpose to illustrate the preparation of pyrethroids from the compounds of the invention and the insecticidal activity of the pyrethroids thus obtained)

Preparation of the 3-phenoxybenzyl ester of (±)-cis, trans-2,2-dimethyl-3-($\beta$-fluoro-$\beta$-trifluoromethyl-vinyl)-cyclopropaneocarboxylic acid and partial separation of the geometric isomers 9.5 g of 2,2-dimethyl-3-($\beta$-fluoro-$\beta$-trifluoromethyl-vinyl)-cyclopropanecarboxylic acid (compound c, Table 2) were converted to the chloride of the acid by treatment with 9.7 g of $PCl_5$ in 200 ml of $CCl_4$, at 23°–24° C. By distillation under vacuum there were gathered 6.2 g of chloride of the acid. (Elemental analysis: Chlorine: found = 14.29%; theoretical = 14.49%).

2.2 g of the chloride of the acid thus obtained were esterified by treatment with 2.2 g of 3-phenoxybenzyl alcohol in 100 ml of anhydrous benzene containing 2 ml of pyridine, at the temperature of 18°–24° C.

After filtering of the pyridinium chlorohydrate, the solution was washed with 80 ml of an aqueous solution of HCl, then with water at 0° C. up to attaining a neutral pH. After anhydration, the solvent was evaporated under vacuum, thereby obtaining 4.1 g of raw 3-phenoxybenzyl ester of the 2,2-dimethyl-3-($\beta$-fluoro-$\beta$-trifluoromethyl-vinyl)-cyclopropanecarboxylic acid.

For achieving a partial separation of the geometrical isomers the product thus obtained was eluted on a column of silica gel with a mixture of n-hexane-benzene (2:1), thereby gathering the following fractions:
I fraction: sample 1-A (1 g)
II fraction: sample 1-M (0.6 g)
III fraction: sample 1-B (1.2 g).

According to the Nuclear Magnetic Resonance analysis, sample 1-A turned out to consist essentially (at least 90%) of the isomer 3-phenoxybenzyl ester of (±)

cis-2,2-dimethyl-3-(β-fluoro-β-trifluoromethyl-E-vinyl)-cyclopropanecarboxylic acid.

Sample 1-B proved to consist prevailingly (at least 80%) of the isomer 3-phenoxybenzyl ester of (±)-trans-2,2-dimethyl-3-(β-fluoro-β-trifluoromethyl-E-vinyl)-cyclopropanecarboxylic acid.

Sample 1-M proved to consist of a mixture of the two above specified isomers in a cis/trans ratio of about 1:3. The characteristics of these samples are recorded in Table 3.

TABLE 3

| Structure | NMR (δ, ppm)[1] |
|---|---|
| Sample 1-A | 2 (m, H$_A$ and H$_B$)<br>6.1 (dd, H$_C$)<br>1.23 (s, CH$_3$)<br>5.06 (s, CH$_3$)<br>6.8–7.5 (m, aromatic protons)<br>J (H$_C$, H$_A$) = 9 Hz<br>J (H$_C$, F trans) = 33 Hz |
| Sample 1-B | 1.7 (d, H$_B$)<br>2.33 (dd, H$_A$)<br>5.23 (dd, H$_C$)<br>1.16 (s, CH$_3$)<br>1.25 (s, CH$_3$)<br>5.05 (s, CH$_2$)<br>6.8–7.4 (m, aromatic protons)<br>J (H$_C$, H$_A$) = 9 Hz<br>J (H$_A$, H$_B$) = 5 Hz<br>J (H$_C$, F trans) = 31 Hz |

NOTE:
[1] s = singlet, d = doublet, dd = doublet of doublet, m = multiplet, J = coupling constant The insecticidal activity of the three samples has been determined in the following way:

Pot-grown potato plants were infested with 4-days old larvae of Leptinotarsa D and subjected to besprinkling with an aqueous dispersion of the products under examination. The mortality percentage (untreated plants=0), was determined 48 hours after the treatment.

In TABLE 4 the insecticidal activities of three samples on Leptinotarsa D., expressed as mortality percentage of the insects exposed to pre-established doses of the product, are set forth.

TABLE 4

Insecticidal activity of the samples on Leptinotarsa D., at a dose of 0.01%(% mortality).

| Sample | Percent mortality |
|---|---|
| 1-A | 100 |
| 1-B | 100 |
| 1-M | 100 |

We claim:

1. A compound having the formula:

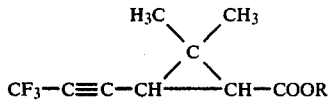

wherein R is selected from the group consisting of H and C$_2$H$_5$.

2. A compound according to claim 1 and which is 2,2-dimethyl-3-(trifluoromethyl-ethynyl)-cyclopropanecarboxylic acid.

3. A compound according to claim 1 and which is ethyl ester of 2,2-dimethyl-3-(trifluoromethyl-ethynyl)-cyclopropanecarboxylic acid.

* * * * *